United States Patent [19]  
Kivlen

[11] Patent Number: 4,904,604  
[45] Date of Patent: Feb. 27, 1990

[54] HYDROCARBON MIXTURE ANALYSIS

[76] Inventor: John A. Kivlen, 4 Hopscotch La., Savannah, Ga. 31411

[21] Appl. No.: 124,273

[22] Filed: Nov. 23, 1987

[51] Int. Cl.$^4$ ............................................. G01N 25/20
[52] U.S. Cl. .................................... 436/140; 436/141; 436/139; 436/144; 436/142
[58] Field of Search ................................ 436/139–144; 422/78, 62; 23/293 R; 73/23

[56] References Cited

U.S. PATENT DOCUMENTS

| | | |
|---|---|---|
| 3,824,388 | 7/1974 | Cugini . |
| 4,153,415 | 5/1979 | Espitalie et al. . |
| 4,229,181 | 10/1980 | Espitalie et al. . |
| 4,231,753 | 11/1980 | Stewart . |
| 4,236,218 | 11/1980 | Killebrew, Jr. et al. . |
| 4,318,178 | 3/1982 | Stewart et al. . |
| 4,325,907 | 4/1982 | Dembicki, Jr. et al. . |
| 4,352,673 | 10/1982 | Espitalie et al. . |
| 4,371,944 | 2/1983 | Stewart et al. . |
| 4,397,958 | 8/1983 | Vroom . |
| 4,400,784 | 8/1983 | Funk et al. . |
| 4,419,328 | 12/1983 | Walsh . |
| 4,519,983 | 5/1985 | Espitalie et al. . |

Primary Examiner—Barry S. Richman  
Assistant Examiner—T. J. Wallen  
Attorney, Agent, or Firm—Cushman, Darby & Cushman

[57] ABSTRACT

A method and/or system for rapidly determining the average composition and characteristics of a hydrocarbon mixture comprising thermally cracking the mixture to form a gaseous product, measuring the ratios or proportions of the individual components in the gaseous product, and comparing the ratios of the components present in the gaseous products with a known property of the hydrocarbon feed mixture and obtaining the average composition and intrinsic properties of the hydrocarbon feed.

8 Claims, 1 Drawing Sheet

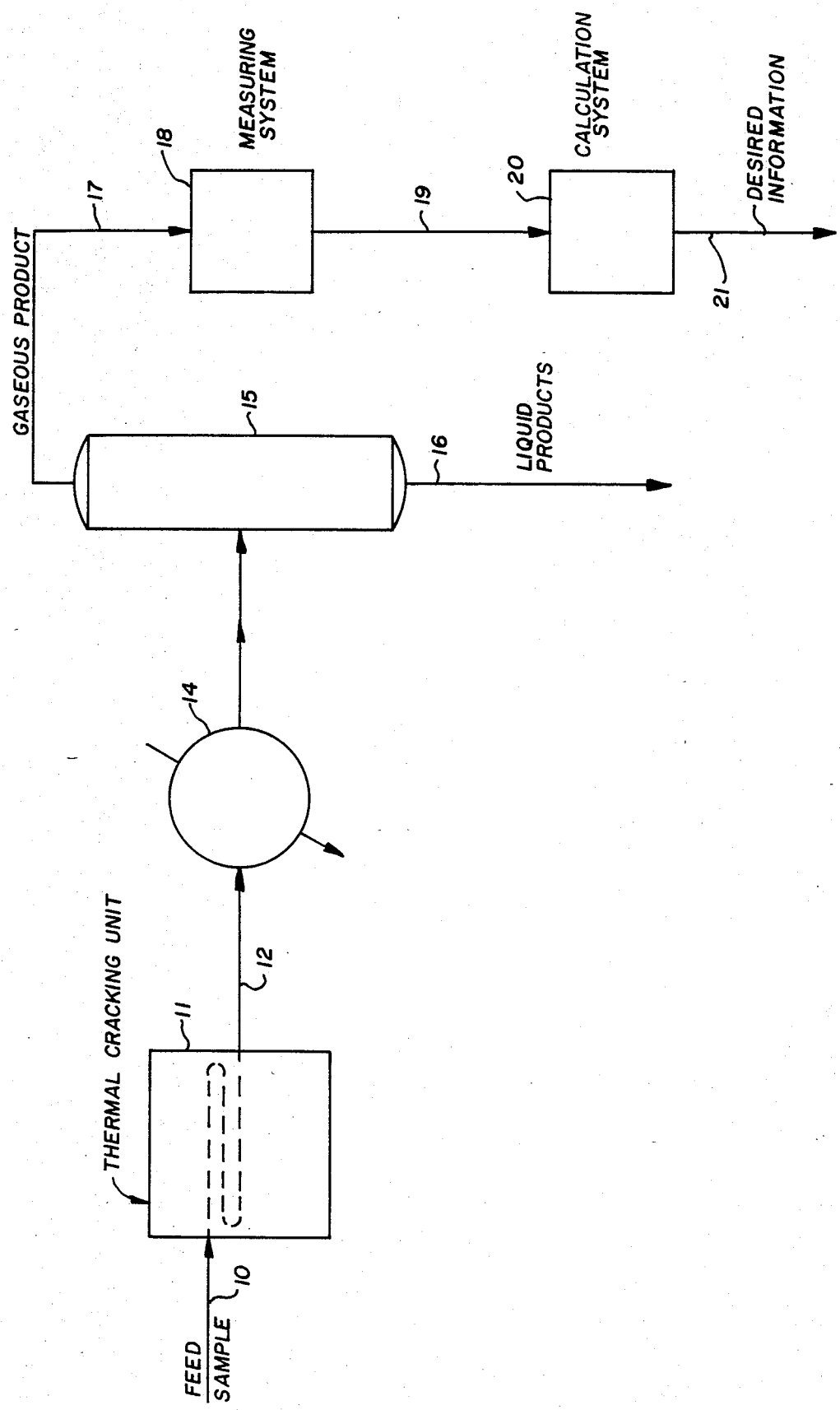

HYDROCARBON MIXTURE ANALYSIS

This invention relates to the a method and system for determining the average composition and characteristics of hydrocarbon mixtures. In accordance with one aspect, this invention relates to a method of determining the average composition and characteristics of a hydrocarbon mixture comprising cracking a sample of the hydrocarbon mixture to form a gaseous product, measuring the ratios or proportions of the individual components in the gaseous product, comparing the ratios of the components present in the gaseous product with a known property of the hydrocarbon mixture prior to cracking, and obtaining the average composition and intrinsic properties of the hydrocarbon mixture.

BACKGROUND OF THE INVENTION

The separation and further treatment of crude oil fractions into the numerous products that are used by the industrial world comprises one of the world's largest industries. In general, the processing of crude oil into the many end products needed by modern society is referred to as the petroleum refining and petrochemical businesses. Most often, the objective of the crude separation and treatment steps involved in these businesses is to ultimately provide hydrocarbon products having particular characteristics, these characteristics normally being dependent on the average composition and other intrinsic compositional factors such as average molecular weight and hydrogen content of these streams.

The specific processing steps utilized in the refining and petrochemical businesses can often be carried out in a more optimal and efficient fashion if the average composition, namely the proportions of iso-paraffins, normal-paraffins, olefins, naphthenes and aromatics along with the average molecular weight and average hydrogen content of the hydrocarbon streams, being treated and/or produced, can be quickly determined such that processing conditions can be regulated and modified to produce the most desirable products. Also, it is often economically desirable to select or blend available hydrocarbon streams based on their average composition and characteristics to produce a more optimum and valuable product.

The measurement of the average composition and characteristics of hydrocarbon mixtures is often difficult and time consuming, with the difficulty and time required for such measurement increasing drastically for hydrocarbon mixtures boiling above about 300 degrees Fahrenheit. While the measurement of average composition and characteristics of higher boiling hydrocarbon mixtures is possible, the time required for such measurement by normal laboratory procedures involves many hours or even days. This is a distinct problem, since many of the processes involved in these businesses utilize and produce hydrocarbon mixtures boiling either entirely or in part above 300 degrees Fahrenheit and, if the time required to measure the average composition of the feed or products is excessive, then timely control of the process to obtain the desired products is impractical or at least less efficient.

It has long been known by those skilled in the processes used for converting hydrocarbon mixtures of one composition to hydrocarbon mixtures of another composition that the final composition is most usually dependent on the initial composition as well as on the operating conditions of the particular process. Some examples of typical processes commonly used to change the composition of crude oil derived hydrocarbon mixtures in the petroleum refining and petrochemical businesses include catalytic cracking, catalytic reforming, thermal reforming, visbreaking, coking, hydrodesulphurization, isomerization, dehydrogenation, steam reforming, et al.

In any and all of these processes, as well as many others, the composition characteristics and value of the products produced are very dependent among other things, on the composition and characteristics of the hydrocarbon streams fed to the processing unit, and it would be economically advantageous to be able to quickly and readily define the average composition and characteristics of the feed and, in many cases, the products, such that the most optimum feed could be selected and the most economic operating conditions could be used.

OBJECTS OF THE INVENTION

An object of this invention is therefore to provide a relatively simple and quick means of defining the hydrogen content, molecular weight, and iso-paraffin, normal-paraffin, olefin, naphthene and aromatics proportions of hydrocarbon mixtures.

A further object of the invention is to provide a more efficient rapid method and/or means for determining properties of complex hydrocarbon mixtures.

The advantages of this invention will be apparent to anyone skilled in the art after reading the specification and claims.

SUMMARY OF INVENTION

In accordance with this invention, there is provided a technique for ascertaining the important average composition and characteristics of crude oil derived hydrocarbon mixtures whereby a sample of the mixture for which the composition and characteristics are to be determined is heated to a temperature which will cause the mixture to thermally react and crack into light hydrocarbons, the lower boiling proportions of which can be readily measured by gas chromatography or mass spectroscopy or other similar means, and the ratios of these proportions of cracked products, in combination with easily obtainable boiling characteristics of the hydrocarbon mixture before the cracking occurred.

Further, in accordance with the invention, the average composition and intrinsic properties of a hydrocarbon mixture is determined by thermally cracking a sample of the hydrocarbon mixture under conditions of temperature and contact time sufficient to produce a gaseous fraction containing acetylene, methane, ethane, ethylene and propylene, measuring the proportions of each of the components in the gaseous fraction, comparing the proportions of the components in the gaseous fraction with a known property such as average boiling range of the hydrocarbon feed mixture, and obtaining a comparative value representative of the average composition and intrinsic properties of the feed hydrocarbon mixture.

DETAILED DESCRIPTION OF INVENTION

It has been found that when hydrocarbon mixtures are thermally cracked, the distribution of the lower molecular weight products resulting from the cracking are dependent on both the average composition and key characteristics of the material being cracked as well as the cracking conditions. It is also well known that thermal cracking of hydrocarbons produces numerous low molecular weight cracking products, and the proportionality or ratio of these cracking products to each other can easily be measured by gas chromatography or mass spectroscopy or other similar means. Uniquely, however, it has been found that the proportionality or ratios of cracked products to each other are not random but are truly dependent on the feed composition and cracking conditions in a manner such that, if one accurately measures five key ratios, or four ratios and some easily obtained feed characteristic such as boiling range, one can accurately relate these measured values to the average feed composition and characteristics and, if desired, can also relate them to the key cracking conditions effecting the product distribution.

It is certainly an unexpected and valuable finding that when hydrocarbon mixtures are thermally cracked there is a unique relationship between the low molecular weight products of cracking and the average composition and characteristics of the hydrocarbon mixture and that this relationship has only five degrees of freedom.

As an example of how this finding can be utilized, it has been further found that if one measures the ratios of acetylene, ethylene, ethane and propylene, each to methane, produced through the thermal cracking of a hydrocarbon mixture and also measures the boiling range of the initial uncracked hydrocarbon mixture, one can accurately relate these measured values to the average composition, namely the iso-paraffin, normal-paraffin, olefin, naphthene and aromatic content, as well as the average molecular weight and hydrogen to carbon ratio or hydrogen content of the uncracked hydrocarbon mixture, and that this relationship can be developed such that it is independent, within reasonable limits, of the conditions under which the thermal cracking takes place. Since with suitable temperatures significant thermal cracking of hydrocarbon mixtures can be carried out in less than one second, and the measurement of the ratios of low molecular weight products of cracking as well as the measurement of the boiling characteristics of the material being thermally cracked can be accomplished in a few moments, it is apparent that this technique provides an extremely rapid means of determining the average composition and characteristics of any crude oil derived hydrocarbon mixture.

The conditions of temperature and contact time for carrying out thermal cracking of the feed hydrocarbon mixture according to the invention can vary appreciably depending upon the particular feed mixture being subjected to thermal cracking. However, the conditions of temperature and contact time will be sufficient to crack the hydrocarbon feed mixture into a gaseous product containing acetylene, methane, ethane, ethylene and propylene. Generally, the temperature of carrying out the cracking operation will be at least 700° C. and no more than 1000° C., with a contact time ranging from about 0.01 seconds to no more than about 10 seconds. In a preferred embodiment of the invention, the cracking temperature ranges from about 750 to about 900° and the contact time ranges from about 0.01 to about 1.0 second, more preferably about 0.1 to about 1 second.

The invention will be properly understood and other advantages thereof will be made apparent from the following description of a non-limitative embodiment, illustrated by the accompanying drawing wherein:

BRIEF DESCRIPTION OF THE DRAWING

FIG. 1 schematically illustrates one embodiment according to the invention.

DETAILED DESCRIPTION OF THE DRAWING

Referring now to the drawing, the process can be carried out by passing the hydrocarbon mixture in line 10 for which the average composition and characteristics are to be determined, either separately or in admixture with an inert diluent, such as argon water or helium, through a heated segment of tubing or pipe of a suitable alloy material in cracking unit 11 such that the temperature of the hydrocarbon mixture is raised to between about 700 to about 1000 degrees Centigrade, and the flow rate and pipe or tubing size selected such that the time interval between the entrance of the hydrocarbon mixture into the heated portion of pipe or tubing in cracking unit 11, and the exit of the reaction products in line 12 from this heated portion can be in the range of about 0.01 to about 10 seconds.

Means for controlling and programming the thermal cracking unit 11 can be provided. They have not been shown so as to not complicate the drawing but their realization only requires ordinary skill.

The sample to be cracked and analyzed can be of any suitable size depending upon the size of the cracking unit, cooling means, and separation device. For practical reasons, the sample is preferably of small size and can be cracked and analyzed without preliminary treatment.

A cooling means 14 and separator 15 are provided whereby the reaction products are cooled and the high molecular weight liquid reaction products separated are removed by line 16 from the low molecular gaseous reaction products removed overhead from separator 15 by line 17 such that the proportions or ratios of the low molecular weight reaction products can be measured by gas chromatography or mass spectroscopy or other suitable means in measuring system 18. Generally, the effluent from thermal cracking is cooled in exchange 14 to a temperature in the range of about 0° to about 150° C.

Normally, the measured ratios of products obtained in measuring system 18 would then be inputted by 19 to a computer or other calculation device 20 whereby the desired properties of the initial hydrocarbon mixture can be calculated using either five measured ratios of reaction products or four ratios and some easily measured property of the initial hydrocarbon mixture such as average point. The resulting information is obtained in 21 and utilized to determine steps to be taken for processing the original hydrocarbon mixture.

The computer or calculator algorithms used for the calculation of the desired properties of the initial hydrocarbon mixture can be easily developed by merely thermally cracking, as described above, a series of hydrocarbon mixtures whose initial properties are measured by normal time consuming laboratory procedures and relating the initial properties to the five ratios of gaseous products produced or alternately four ratios of gaseous products and an easily obtained uncracked hydrocarbon property. The accuracy of the algorithm will of course be dependent on the number of samples tested as well as the skill of the individuals developing said algorithm. However, with the knowledge provided in the specifications and claims of this patent, namely the degrees of freedom and the fact that a unique relationship exists between the ratios of light gaseous products of thermal cracking and the composition and properties of the hydrocarbon thermally cracked, anyone skilled in the art can easily develop the desired algorithms.

SPECIFIC EXAMPLE

The following example shows how the concepts emobodied in the description and claims of this patent application were used to achieve a rapid analysis of samples of crude derived hydrocarbon mixtures.

Initially, 25 samples of crude derived hydrocarbon mixtures were obtained and a portion of each sample analyzed in a laboratory. The samples varied from very light naphthas to heavy vacuum distilled gas oils. The laboratory analysis defined the following physical and chemical properties of each sample;
  a. The molal average boiling point (mabp) derived from an ASTM distillation.
  b. The weight % of normal pararffins (npara), iso paraffins (ipara), naphthenes (naph) and aromatics (arom).
  c. The average hydrogen content (hyd).
  d. The average molecular weight (mwt).

As stated earlier these analysis were expensive and time consuming, with the typical time required for a single analysis being more than 48 hours of elapsed time. However the techniques used were straight forward and can be carried out by anyone skilled in the laboratory procedures normally used for such analysis.

Remaining portions of twenty of the original twenty five samples were then randomly selected and further portions of each of these samples were passed through a thermal cracking device consisting of a two foot long segment of 3/16th inch inside diameter stainless tubing, such tubing being heated to a temperature of between 825 and 875 degrees centigrade. After exiting the heated tubing, the cracked products of each sample were then cooled to approximately 110 degrees centigrade and the gaseous and liquid cracked products separated from each other. The gaseous products were then passed into a gas chromatograph where the ratios of methane, acetylene, ethylene, ethane, and propylene to each other were measured and recorded along with an identifying number representing the particular sample. Two separate portions of each of the twenty samples were thermally cracked and the ratios of the five above named components to each other measured and recorded. Another portion of each sample was then submitted to a Hallikainen distillation analyzer where its molal average boiling point was determined and recorded.

For each of the twenty samples cited above, the data obtained from the analysis of the cracked products, the distillation analysis and the laboratory analysis of the physical and chemical properties were compiled and imput to a computer. Equations were then generated by regressing desired physical and chemical properties against the cracked product ratios and the average boiling point. The regressions were carried out using a micro computer and the program "SYSTAT". The program and techniques for regression are available and well understood by anyone skilled in the art.

Based on the results of the regressions described above the following computer program was written in the "basic" language.

```
10 LTM(L) = -.4343*LOG((ETH(L)*SEL(L)) / (SEV (L) *MABP(L)))
```

```
20 PNPARA(L) = 231.439 -85.829*SEV(L) *SEL(L)
+229.795*SEV(L) -199.742*SEL(L) -11480.429#*ACET(L)
*ACET(L) *ETH(L)
-17.644*LTM(L) *LTM(L) -232.579*(SEV(L) /SEL(L))
+22.291*SEV(L)*SEV(L) +42.337*SEL(L) *SEL(L)
+.072*MABP(L)
30 IF PNPARA(L) <0 THEN PNPARA(L) = 0
40 PIPARA(L) = 91.247 +5.462*SEV(L) *SEL(L)
-111.847*SEL(L) -64.68801*ETH(L)
+41.122*LTM(L)*LTM(L)
-12.005*LTM(L)*LTM(L)*LTM(L) +31.475*SEL(L) *SEL(L)
-3.359*SEL(L) *SEL(L) *SEL(L)
50 IF PIPARA(L) <.01 THEN PIPARA(L) = 0
60 YLB(L) = (SEL(L)-SEV(L)) / (SEV(L) +SEL(L) + (1/SEV(L)) + (1/SEL(L))
+ (SEV(L) /SEL(L)) +(SEL(L)/SEV(L))
70 PNAPH(L) = -13.1 +68.39*ETH(L) -20.38*LTM(L)
*LTM(L) +11.363*LTM *LTM(L) *LTM(L) +107.968*YLB(L)
-2.355*SEL(L) *SEL(L) -.173*MABP(L)
80 IF PNAPH(L) < .01 THEN PNAPH(L) = 0
90 PAROM(L) = -20.739 +15.591*SEV(L) *SEL(L)
+24.509*SEL(L)-21.674*ETH(L) -8.932*SEV(L) *SEV(L)
-11.223*SEL(L) *SEL(L) +.089*MABP(L)
100 IF PAROM(L) < .01 THEN PAROM(L) = 0
110 IF PNPARA(L) > 100 THEN PNPARA(L) = 100
120 IF PIPARA(L) > 100 THEN PIPARA(L) = 100
130 IF PNAPH(L) > 100 THEN PNAPH(L) = 100
140 IF PAROM(L) > 100 THEN PAROM(L) = 100
150 TOT(L) = 100/(PNPARA(L) +PIPARA(L) +PNAPH(L) +PAROM(L))
160 PNPARA(L) = PNPARA(L) *TOT(L)
170 PIPARA(l) = PIPARA(L) *TOT(L)
180 PNAPH(L) = PNAPH(L) *TOT(L)
190 PAROM(L) = PAROM(L) *TOT(L)
200 PFDHYD(L) = 13.005 -2.457*(MABP(L) /100)
+.791*(MABP(L) /100) 2 -.085*(MABP(L)/100)
3+.0452*PNPARA910
+.0452*PIPARA(L) +.03*PNAPH(L)
210 MWTI(L) = 59.5 +.422*MABP(L)
-.09064* ((MABP(L) *MABP(L)) /1000)
+2.11* ((MABP(L) 3) /1000000!)
220 MWT2(L) = .00216*PIPARA(L)*MWT1(L)
-.001978*PNAPH(L)*MWT1(L) +.002176*PAROM(L)*
MWT1(L)
230 PMWT(L) = MWT1(L) +MWT2(L)
```

Where the following terms define the ratios of the cracked products which are measured as described above and input to the program;

SEV(L)=THE RATIO - PROPYLENE/METHANE

SEL(L)=THE RATIO - ETHYLENE/METHANE

ETH(L)=THE RATIO - ACETYLENE/METHANE

ACET(L)=THE RATIO - ACETYLENE/METHANE

And the following term defines the boiling characteristic of the sample being tested as described above and also imput to the program;

MABP(L)=THE MEAN AVERAGE BOILING POINT

And the following terms define the chemical and physical characteristics of the sample predicted by the program.

PNPARA(L)=THE PREDICTED NORMAL PARAFFIN CONTENT

PIPARA(L)=THE PREDICTED ISO PARAFFIN CONTENT

PNAPH(L)=THE PREDICTED NAPHTHENE CONTENT

PAROM(L)=THE PREDICTED AROMATIC CONTENT

PFDHYD(L)=THE PREDICTED HYDROGEN CONTENT

PMWT(L)=THE PREDICTED AVERAGE MOLECULAR WEIGHT

To indicate the effectiveness of this program, the five remaining samples which were analyzed in the laboratory were thermally cracked under the same range of conditions and in the same apparatus as described above. The final or fifth sample was in fact divided into two separate and smaller samples and each thermally cracked at somewhat different temperatures. The ratios of cracked products and the boiling characteristic were then imput to the above computer program and predictions made as to the physical and chemical properties of each sample. These predicted properties were compared with those measured in the laboratory. The following table shows a comparison of the predicted and measured values;

| Sample | normal paraffin content | | Iso paraffin content | |
|---|---|---|---|---|
| | measured | predicted | measured | predicted |
| 1 | 16.5 | 16.7 | 16.5 | 15.1 |
| 2 | 12.2 | 15.2 | 13.3 | 12.7 |
| 3 | 33.8 | 34.2 | 29.9 | 31.3 |
| 4 | 38.6 | 37.8 | 30.5 | 30.6 |
| 5a | 57.3 | 58.4 | 28.7 | 26.0 |
| 5b | 57.3 | 59.6 | 28.7 | 25.4 |

| Sample | Naphthene content | | Aromatics content | |
|---|---|---|---|---|
| | measured | predicted | measured | predicted |
| 1 | 38.6 | 39.7 | 28.4 | 28.7 |
| 2 | 35.0 | 35.3 | 39.5 | 36.1 |
| 3 | 25.8 | 24.2 | 10.5 | 11.3 |
| 4 | 17.9 | 19.5 | 13.1 | 12.5 |
| 5a | 10.0 | 11.8 | 4.0 | 3.7 |
| 5b | 10.0 | 10.4 | 4.0 | 4.2 |

| Sample | Wt. % Hydrogen | | Molecular weight | |
|---|---|---|---|---|
| | measured | predicted | measured | predicted |
| 1 | 13.00 | 13.09 | 260 | 255 |
| 2 | 12.69 | 12.76 | 322 | 327 |
| 3 | 15.00 | 14.94 | 104 | 106 |
| 4 | 14.65 | 14.84 | 108 | 111 |
| 5a | 16.04 | 16.03 | 83 | 85 |
| 5b | 16.04 | 16.02 | 83 | 86 |

As can be seen from this example the physical and chemical properties of a hydrocarbon mixture can be quickly and accurately predicted using four ratios of light hydrocarbon components resulting from thermally cracking the mixture along with a measurement of the boiling characteristics of the mixture, and that the accuracy of the prediction of these physical and chemical properties is well within the accuracy of rigorous laboratory test methods. It will also be obvious to those skilled in the art that the overall accuracy of any mathematical or computer model for predicting the physical and chemical properties of hydrocarbon mixtures, developed using the techniques described herein, will increase if a larger number of samples are tested and the data regressed and used in the development of the mathematical or computer model.

What is claimed is:

1. A method for determining, in a timely manner consistent with real time control of a chemical or petrochemical process, the characteristics of a crude derived feed hydrocarbon mixture, which comprises
   (a) thermally cracking a crude derived feed hydrocarbon mixture by heating to an elevated temperature for a period of time sufficient to form a gaseous fraction containing components comprising acetylene, methane, ethane, propane, ethylene, and propylene,
   (b) selecting a component from the gaseous fraction from step (a) and measuring the compositional ratios of five other components of the gaseous fraction each to the selected component to obtain five measured ratios, and
   (c) determining one or more of the feed hydrocarbon mixture characteristics selected from the group consisting of normal paraffin content, isoparaffin content, naphthene content, olefin content, aromatic content, hydrogen content, average molecular weight, and viscosity based upon the five ratios obtained in step (b).

2. A method according to claim 1 wherein the thermally cracked product of step (a) is cooled sufficiently to form a liquid fraction which is separated from a remaining gaseous fraction prior to measuring the proportions or ratios of the individual components of the gaseous fraction in step (b).

3. A method according to claim 1 wherein an inert diluent is mixed with the feed hydrocarbon mixture being subjected to thermal cracking.

4. A method according to claim 1 wherein the temperature obtaining during thermal cracking ranges from about 700° to about 1000° C.

5. A method according to claim 4 wherein the contact time of hydrocarbon being cracked ranges from about 0.01 seconds to about 10 seconds.

6. A method according to claim 2 wherein cooling is effected at a temperature in the range between about 0° and about 150° C.

7. A method according to claim 1 wherein said temperature of cracking ranges from about 750° to said 900° C. and the period of contact of hydrocarbon being cracked ranges from about 0.01 to about 1 second.

8. A method for determining, in a timely manner consistent with real time control of a chemical or petrochemical process, the characteristics of a crude derived feed hydrocarbon mixture, which comprises
   (a) thermally cracking a crude derived feed hydrocarbon mixture by heating to an elevated temperature for a period of time sufficient to form a gaseous fraction containing components comprising acetylene, methane, ethane, propane, ethylene, and propylene,
   (b) selecting a component from the gaseous fraction from step (a) and measuring the compositional ratios of four of the five other components each to the selected component, and measuring the average boiling point of the feed hydrocarbon mixture, and
   (c) determining one or more of the feed hydrocarbon mixture characteristics selected from the group consisting of normal paraffin content, isoparaffin content, naphthene content, olefin content, aromatic content, hydrogen content, average molecular weight, and viscosity based upon the four ratios and the average boiling point obtained in step (b).

* * * * *